US006875296B2

(12) United States Patent
Bolyard, Jr. et al.

(10) Patent No.: US 6,875,296 B2
(45) Date of Patent: Apr. 5, 2005

(54) VARIABLE SPACING STRAND COATING METHOD

(75) Inventors: Edward W. Bolyard, Jr., Old Hickory, TN (US); Daniel D. Bourget, Hendersonville, TN (US); Mairi C. MacLean, Hendersonville, TN (US)

(73) Assignee: Illinois Tool Works Inc., Glenview, IL (US)

( * ) Notice: Subject to any disclaimer, the term of this patent is extended or adjusted under 35 U.S.C. 154(b) by 383 days.

(21) Appl. No.: 10/147,188

(22) Filed: May 16, 2002

(65) Prior Publication Data

US 2002/0134491 A1 Sep. 26, 2002

Related U.S. Application Data

(62) Division of application No. 09/621,721, filed on Jul. 24, 2000, now Pat. No. 6,520,237.

(51) Int. Cl.[7] .......................... B32B 31/00; A61F 13/16

(52) U.S. Cl. ....................... 156/161; 156/163; 156/164; 427/207.1; 427/208.4; 427/208.6; 427/421; 427/422; 427/424

(58) Field of Search ................................ 156/161, 163, 156/164, 494, 495, 496, 578; 427/207.1, 208.4, 208.6, 421, 422, 424

(56) References Cited

U.S. PATENT DOCUMENTS 4,687,477 A 8/1987 Suzuki et al.
4,750,960 A 6/1988 Bubeck
5,049,721 A * 9/1991 Parnas et al. .......... 219/121.68
5,525,175 A * 6/1996 Blenke et al. .............. 156/161
5,660,664 A * 8/1997 Herrmann ................... 156/161
5,766,411 A 6/1998 Wilson
5,964,973 A 10/1999 Heath et al.
6,077,375 A 6/2000 Kwok
6,197,406 B1 * 3/2001 Kwok ..................... 428/195.1

FOREIGN PATENT DOCUMENTS

EP 475419 A1 * 12/1991
WO WO-97/17921 A1 * 5/1997

OTHER PUBLICATIONS

ITW Dynatec Integra "Elastic Strand Coating System", pp. 1–4, copyright 1998.*

Nordson Corp., "Non–Woven Systems" (9) website pages, 1998.

* cited by examiner

*Primary Examiner*—Jeff H. Aftergut
(74) *Attorney, Agent, or Firm*—Donald J. Breh; Mark W. Croll; Paul F. Donovan

(57) ABSTRACT

Strand coating methods having an applicator head pivotally mounted adjacent a substrate, a coating material dispenser mounted on the applicator head, a strand guide mounted on the applicator head, wherein the strand guide and the coating material dispenser are adjustably positionable in unison relative to the substrate by pivoting the applicator head to vary the spacing of the strands relative to the substrate.

19 Claims, 2 Drawing Sheets

VARIABLE SPACING STRAND COATING METHOD

CROSS REFERENCE TO RELATED APPLICATIONS

The present application is a division of U.S. patent application Ser. No. 09/621,721 filed on 24 Jul. 2000, now U.S. Pat. No. 6,520,237 entitled "Variable Spacing Strand Coating System And Method", the disclosure of which is incorporated by reference herein, assigned commonly with present application, and from which priority under 35 U.S.C. § 120 is claimed.

BACKGROUND OF THE INVENTION

The invention relates generally to strand coating, and more particularly to variable spacing strand coating systems and methods therefor.

An object of the present invention is to provide novel strand coating methods and systems that overcome problems in and improve upon the prior art.

Another object of the invention is to provide in some embodiments thereof novel strand coating methods and systems that are economical.

A further object of the invention is to provide in some embodiments thereof novel strand coating methods and systems that are reliable.

Another object of the invention is to provide in some embodiments thereof novel strand coating methods and systems for variably spacing a plurality of strands.

Another object of the invention is to provide in some embodiments thereof novel strand coating methods and systems for variably spacing a plurality of strands relative to a substrate without changing coating material dispensers or strand guides.

A further object of the invention is to provide in some embodiments thereof novel strand coating methods and systems for variably spacing a plurality of strands without resetting system fluid and air pressure.

Yet another object of the invention is to provide in some embodiments thereof novel strand coating methods and systems for more accurately aligning one or more strands relative to a coating material dispenser.

Another object of the invention is to provide in some embodiments thereof novel strand coating methods and systems that are less susceptible to misalignment.

Still another object of the invention is to provide in some embodiments thereof novel strand coating methods and systems having adjustable strand guides.

Another object of the invention is to provide in some embodiments thereof novel strand coating methods and systems having coating material dispensers with strand guides coupled thereto.

A further object of the invention is to provide in some embodiments thereof novel strand coating methods and systems having coating material dispensers with strand guides coupled thereto that are pivotally adjustable relative to a substrate.

A more particular object of the invention is to provide in some embodiments thereof novel strand coating methods and systems comprising a strand guide having a guiding surface at an angle relative to a moving substrate, a plurality of moving strands disposed side by side over the guiding surface of the strand guide, and a coating material dispenser disposed adjacent the plurality of strands.

Another more particular object of the invention is to provide in some embodiments thereof novel strand coating methods and apparatuses comprising an applicator head pivotally mounted on a support member, a coating material dispenser mounted on the applicator head, a strand guide mounted on the applicator head, whereby the strand guide and the coating material dispenser are adjustably positionable in unison by pivoting the applicator head.

Yet another more particular object of the invention is to provide in some embodiments thereof novel strand coating methods and apparatuses comprising a coating material applicator having a dispenser with at least one orifice, a roller pin extending from a roller arm adjustably coupled to the coating material applicator by a pivot member, and a strand guide roller having a plurality of grooves disposed about a rotation axis thereof, the strand guide roller rotatably coupled to the roller pin.

Still another more particular object of the invention is to provide in some embodiments thereof novel strand coating systems and methods comprising drawing a plurality of strands side by side, in spaced apart relation over a strand guide adjacent a substrate, applying coating material from a coating material dispenser onto the plurality of strands on a downstream side of the strand guide, depositing the plurality of strands with the coating material applied thereto onto the substrate, adjusting a spacing of the plurality of strands on the substrate by changing an orientation of the strand guide relative to the substrate.

These and other objects, aspects, features and advantages of the present invention will become more fully apparent upon careful consideration of the following Detailed Description of the Invention and the accompanying Drawings, which may be disproportionate for ease of understanding, wherein like structure and steps are referenced generally by corresponding numerals and indicators.

DETAILED DESCRIPTION OF THE INVENTION

Figure 1:
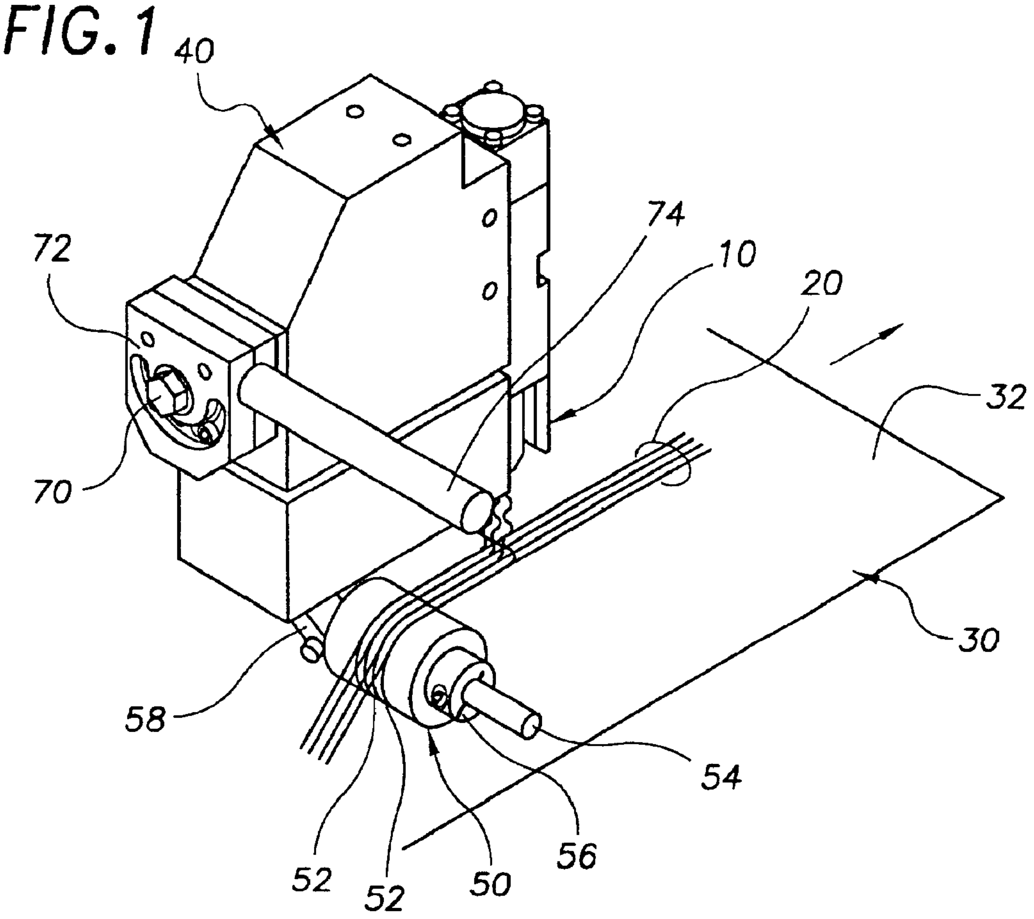
FIG. 1 is a strand coating system according to an exemplary embodiment of the invention.

In FIG. 1, the strand coating system comprises a coating material dispenser 10 that applies a coating material, for example a hot melt adhesive or an atomized substance, onto one or more strands, identified collectively by numeral 20, moving relative thereto.

The strands 20 may, for example, be elastic rubber or Lycra materials used in the manufacture of diapers, incontinence pads and hospital garments. The strands may also be wire or cable, for example fiber optic cable, or some other elongated member onto which it is desirable to deposit a coating material.

Figure 3:
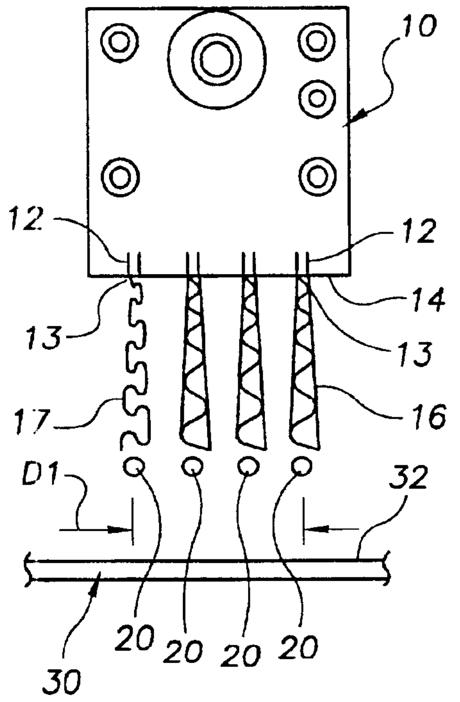
FIG. 3 is a partial view of an exemplary coating material dispenser in a first configuration.

In FIG. 3, the exemplary dispenser 10 includes a plurality of conduits 12, shown only partially and in phantom, terminating at corresponding orifices arranged in a spaced apart series on a side 14 of the dispenser. The orifices of the exemplary dispenser each emit therefrom a corresponding coating material flow 16, which may be a substantially continuous or discrete vacillating filament or an atomized spray, toward a corresponding strand in alignment with the orifice.

In FIG. 3, some of the orifices 13 are illustrated schematically at the origin of the corresponding flows 16 spaced apart evenly in a single row on the dispenser. The orifices may be recessed or protrude from the side 14 of the dispenser. In other embodiments, the spacing between adjacent orifices is not necessarily the same. Alternatively, there may be more than one row or series of orifices arranged in alignment with the direction of the strand so that more than one orifice dispenses coating material onto each strand. In other embodiments, the orifices of adjacent rows may be offset.

Coating material dispensers suitable for use with the present invention are disclosed for example in U.S. Pat. No. 5,902,540, entitled "Meltblowing Method and Apparatus", and U.S. Pat. No. 5,904,298, entitled "Improved Meltblowing Method and System". These preferred exemplary devices are capable of producing filaments and atomized spray patterns that vacillate predominately non-parallel to the axis of the strands and provide precise control over the coating material dispensed therefrom.

In one embodiment, illustrated in FIG. 3, the coating material dispenser 10 dispenses substantially continuous coating material filaments 17 having a repeating, generally omega shaped pattern from the orifices thereof, only one of which is illustrated, as disclosed more fully in co-pending U.S. application Ser. No. 09/143,883 entitled "Omega Spray Pattern And Method Therefor", which is assigned commonly with the present application and is incorporated herein by reference.

In other embodiments, the coating material dispenser may be a spiral spray nozzle having a single orifice that dispenses a corresponding spiral filament onto one or more strands, or alternatively some other coating material dispensing apparatus.

Figure 5:
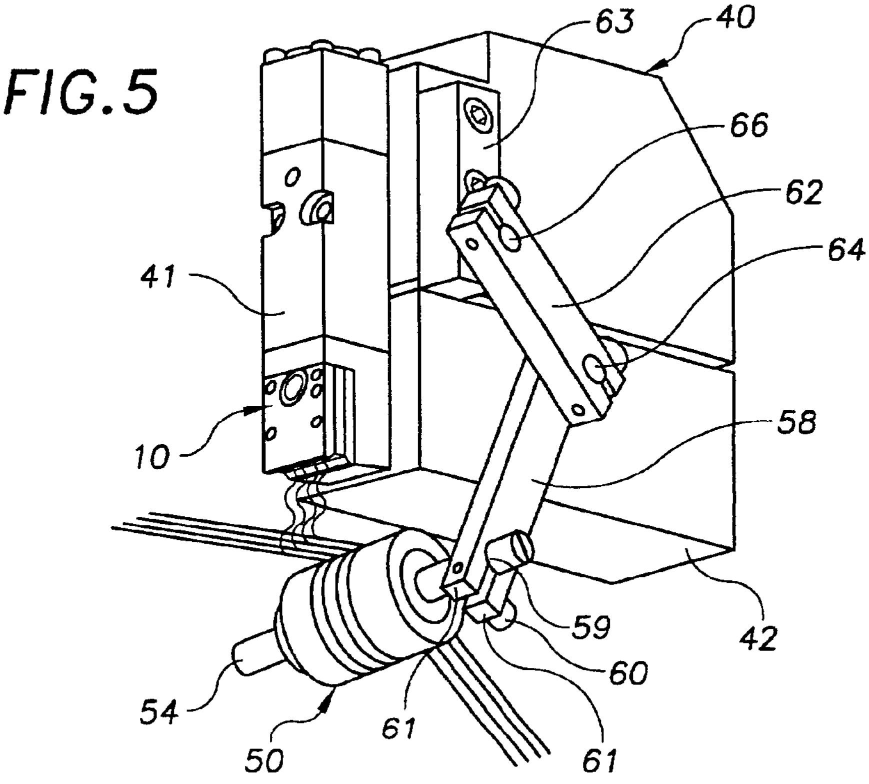
FIG. 5 is another view of an exemplary strand guide mounted to an exemplary strand coating applicator.

In FIG. 5, the exemplary coating material dispenser 10 is coupled to or mounted on an applicator head 40, which supplies coating material and in some embodiments heated air to the coating material dispenser, for example through a nozzle module 41, as is known generally by those having ordinary skill in the art.

In some applications, strands having coating material applied thereto are adhered to or deposited on a substrate moving relative to the coating material dispenser, usually in unison with the strands. The coating material dispenser however may move relative to the one or more strands and any substrate.

A strand guide having a guiding surface is preferably disposed adjacent the coating material dispenser, preferably on an upstream side thereof, to guide the strands past the coating material dispenser. The one or more strands are generally drawn over the guiding surface of the strand guide, which aligns the strands side by side in spaced apart relation relative to corresponding orifices of the coating material dispenser, for dispensing coating material dispensed therefrom onto the strands.

In the exemplary embodiment of FIG. 1, the strand guide is a rotatable roller 50 and the strand guiding surface thereof includes a plurality of spaced apart grooves 52 disposed thereabout. The strands are each disposed in a corresponding groove 52. The spacing of at least some of the grooves generally corresponds with the spacing of the dispenser orifices. In the exemplary embodiment, the roller aligns and guides the strands adjacent a corresponding orifice of the coating material dispenser, as illustrated in FIG. 3. In alternative embodiments, the strand guide may have other configurations besides a channeled roller.

The strand guide is preferably coupled to the coating material dispenser, in fixed relation relative thereto. In the exemplary embodiment, the coating material dispenser and strand guide are both coupled to the applicator head, thereby eliminating or at least substantially reducing any misalignment therebetween, for example misalignment caused by vibrating machinery, as frequently occurs in prior art systems having the strand guide coupled to machinery other than the coating material dispenser.

Figure 2:
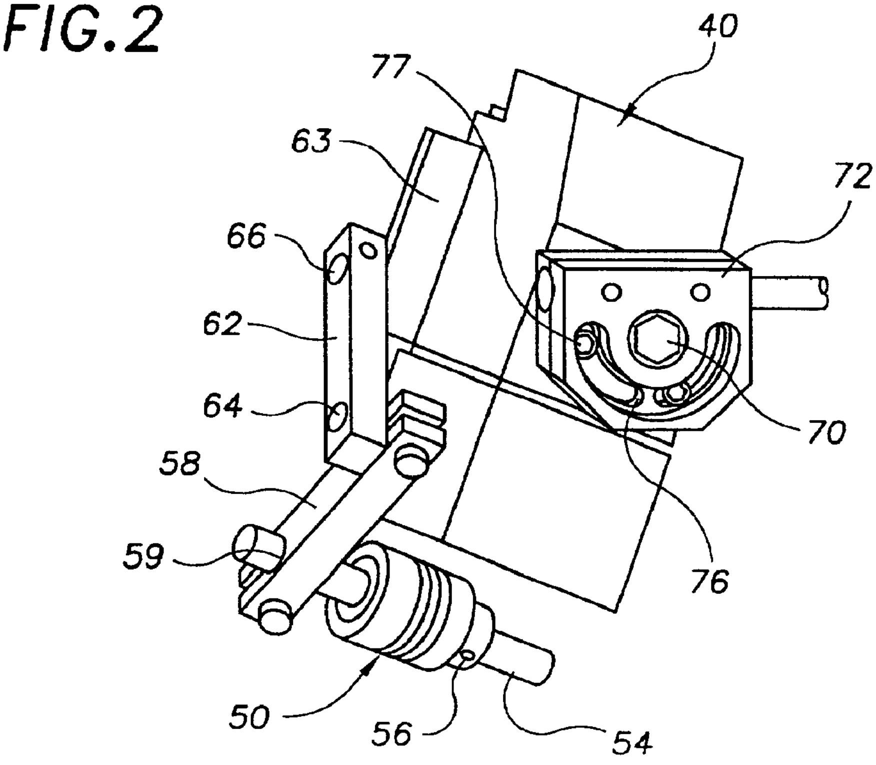
FIG. 2 is a partial view of a strand coating applicator.

In FIGS. 1, 2 and 5, the exemplary roller guide 50 is rotatably coupled to a roller axle or shaft 54, preferably with roller bearings. In FIGS. 1 and 2, the exemplary roller guide 50 is retained on the roller shaft 54 by a collar 56 fastened thereto with a set screw or other fastening means.

In FIGS. 2 and 5, the roller shaft 54 extends from a roller arm 58 adjustably coupled to the applicator head 40. The roller shaft is also preferably adjustably coupled to the roller arm, for example by threaded engagement with a threaded opening 59 of the roller arm 58. In the exemplary embodiment, the roller guide 50 and/or roller shaft 54 is adjustable in either direction along the axis of the shaft 54 to align the guide grooves of the roller 50 relative to the one or more orifices of the coating material dispenser.

In FIGS. 2 and 5, the roller arm 58 is pivotally coupled to a guide arm 62 by a pivot pin 64 extending from one or the other. The guide arm 62 is also preferably adjustably coupled to the applicator, for example by a pivot pin 66 extending from a bracket 63 mounted thereon.

In FIG. 5, the guide roller 50 may be adjustably positioned toward and away from a bottom side 42 the applicator head 40. The guide roller 50 may also be adjustably positioned in the upstream and downstream direction of the strands, closer or farther away from the dispenser.

In the exemplary embodiment of FIG. 5, the roller axle 54 is secured in the opening 59 of the roller arm 58 by a bolt 60 disposed through prongs 61 thereof, which are clamped about the shaft 54 upon tightening the bolt. The guide arm 62 is similarly secured to the pivot pin 66, and the roller arm 58 is similarly secured to the guide arm 62. In other embodiments, the guide roller is adjustably coupled to the applicator head by other structure.

In some embodiments of the invention, the strand guide is adjustably mounted on a pivot member to change the orientation of the guiding surface of the strand guide to vary the spacing of the strands relative to the substrate. The coating material dispenser is preferably adjustable in unison with the strand guide, for example by adjusting the position or orientation of the applicator head, to facilitate application of the coating material onto the strands.

Figure 4:
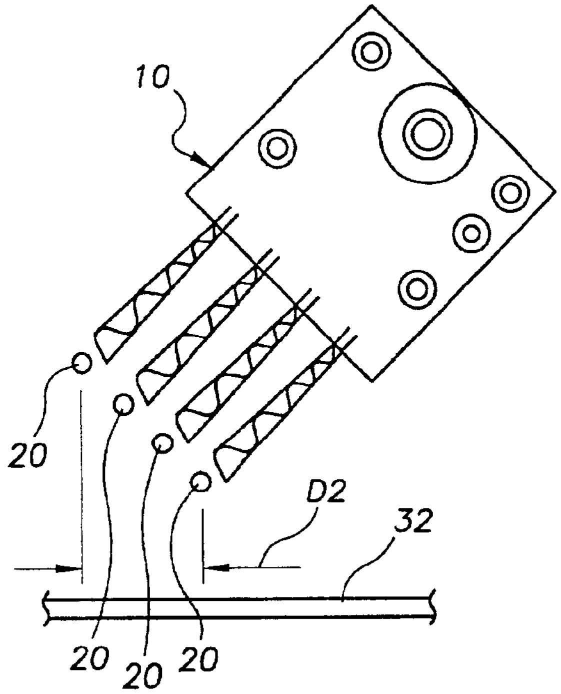
FIG. 4 is another partial view of an exemplary coating material dispenser in a second configuration.

In the exemplary embodiments of FIGS. 3 and 4, spacing between the plurality of strands 20 as they are deposited onto the substrate 30 is varied by changing the orientation of the strand guide, not illustrated, and particularly the guiding surface thereof relative to a surface 32 of the substrate. The plane of the strands 20 corresponds generally to the orientation of the guiding surface of the strand guide relative to the substrate surface 32.

In the embodiment of FIG. 1, the grooved guiding surface of the strand guide 50 is parallel to the substrate surface 32, so that the plane of the strands 20 is also parallel to the substrate, as illustrated best in FIG. 3. The spacing between adjacent strands relative to the substrate surface 32 thus corresponds generally with the spacing between the grooves on the strand guide over which the strands are drawn. In FIG. 3, for example the spacing between the outermost strands is D1.

In FIG. 4, the strand guide has been pivoted to orient the grooved guiding surface thereof at an angle relative to the substrate so that the plane of the strands is at a corresponding angle relative to the substrate. The spacing between adjacent strands relative to the substrate surface 32 is thus reduced in some proportion to the angle between the substrate and the guiding surface of the strand guide over which the strands are drawn. In FIG. 4, the spacing between the outermost strands disposed over an angled strand guide is D2, which is less than the spacing D1 in FIG. 3.

FIGS. 1 and 2 illustrate the applicator head 40 pivotally mounted on a pivot or bolt shaft 70 having an axis substantially transverse to the side by side arrangement of the plurality of orifices, which permits adjustment of the orientation of the coating material dispenser and strands, as illustrated in FIGS. 3 and 4. In FIGS. 3 and 4, the pivot axis of the coating material dispenser and strand guide is aligned substantially in a direction of the moving substrate, which moves into or out of the page of the drawing.

In FIGS. 1 and 2, the pivot shaft 70 extends through a mounting block 72 supported by a support member 74, in the exemplary form of a rod. In FIG. 2, the mounting block 72 includes one or more arcuate slots 76 disposed about the pivot shaft 70. A bolt 77 extends through the corresponding slot 76 and into a threaded bore of the applicator head 40.

Engagement of the bolt 77 with opposite end portions of the slot 76 limits pivoting or rotation of the applicator head 40 about the shaft 70, and engagement of a head portion of the bolt 77 with the mounting block 72 secures the orientation of the applicator head 40 relative thereto upon tightening the bolt 77.

While the foregoing written description of the invention enables one of ordinary skill to make and use what is considered presently to be the best mode thereof, those of ordinary skill will understand and appreciate the existence of variations, combinations, and equivalents of the specific exemplary embodiments herein. The invention is therefore to be limited not by the exemplary embodiments herein, but by all embodiments within the scope and spirit of the appended claims.

What is claimed is:

1. A strand coating method comprising:

drawing a plurality of strands side by side, in spaced apart relation over a strand guide adjacent a substrate;

applying a coating material from a coating material dispenser onto the plurality of strands;

depositing the plurality of strands with the coating material applied thereto onto the substrate;

adjusting a spacing of the plurality of strands on the substrate by changing an orientation of the strand guide relative to the substrate.

2. The method of claim 1, the strand guide is a roller, drawing the plurality of strands over corresponding grooves disposed about the roller, changing the orientation of the strand guide by tilting a rotation axis thereof relative to the substrate.

3. The method of claim 1, the coating material dispenser is mounted on an applicator head and the strand guide is coupled thereto in fixed relation to the coating material dispenser on an upstream side thereof, changing the orientation of the strand guide by pivoting the applicator head.

4. The method of claim 3, the coating material dispenser has a plurality of orifices on a side thereof aligned in a series non-parallel to a moving direction of the substrate, the strand guide is a roller having a plurality of grooves disposed thereabout in alignment with a corresponding one of the orifices, pivoting the applicator head about a pivot member having an axis aligned substantially in the moving direction of the substrate.

5. The method of claim 4, vacillating the coating material filaments dispensed from the orifices of the coating material dispenser with a repeating, generally omega shaped pattern and depositing the vacillating filaments onto a corresponding adjacent strand.

6. A method in a strand coating system having a guide arm pivotally interconnecting a strand guide to a coating material dispenser, the method comprising:

drawing a strand along a strand guiding groove of the strand guide;

dispensing a coating material from an orifice of the coating material dispenser, the orifice of the coating material dispenser spaced apart from the strand, the orifice of the coating material dispenser aligned with the strand guiding groove of the strand guide;

capturing the coating material on the strand.

7. The method of claim 6, adjusting a spacing between the strand and the orifice of the coating material dispenser by pivoting the guide arm.

8. The method of claim 6, the strand guide is a strand guide roller coupled to the coating material dispenser, pivoting the stand guide roller in unison with the coating material dispenser by pivoting the coating material dispenser about an axis substantially transverse to an axis of the strand guide roller.

9. The method of claim 8, the strand guide roller having a plurality of spaced apart strand guiding grooves, the coating material dispenser having a plurality of orifices, each of the orifices aligned with not more than a corresponding one of the strand guiding grooves, drawing each of a plurality of strands along a corresponding strand guiding groove, dispensing coating material from each orifice of the coating material dispenser, capturing coating material on each of the plurality of strands from the orifice aligned with the strand guiding groove along which the strand is drawn.

10. The method of claim 6, vacillating the coating material dispensed from the orifice of the coating material dispenser in a repealing, generally omega-shaped pattern.

11. The method of claim 6, dispensing the coating material substantially continuously.

12. A strand coating method comprising:

drawing a strand over a strand guide, the strand guide coupled to a coating material dispenser by a pivotal guide arm, an orifice of the coating material dispenser spaced apart from the strand;

adjusting a spacing between the strand and the orifice of the coating material dispenser by pivoting the pivotal guide arm.

13. The method of claim 12, the strand guide is a roller having a strand guiding groove, the coating material dispensing orifice of the coating material dispenser aligned with the strand guiding groove, drawing the strand along the strand guiding groove in alignment with the coating material dispensing orifice.

14. The method of claim 12, the strand guide is a strand guide roller, pivoting the stand guide roller in unison with the coating material dispenser by pivoting the coating material dispenser about an axis substantially transverse to an axis of the strand guide roller.

15. The method of claim 14, the strand guide roller having a plurality of spaced apart strand guiding grooves, the coating material dispenser having a plurality of orifices, each of the orifices aligned with not more than a corresponding one of the strand guiding grooves, drawing each of a plurality of strands along a corresponding strand guiding groove in alignment with the corresponding orifice.

16. A strand coating method comprising:

drawing a plurality of strands disposed side by side over a strand guide, the side by side arrangement of the plurality of strands disposed along a dimension of the strand guide, the strand guide coupled to a coating material dispenser, the strands spaced apart from the strand coating material dispenser;

pivoting the stand guide in unison with the coating material dispenser by pivoting the coating material dispenser about an axis substantially transverse to the dimension of the strand guide.

17. The method of claim 16, the strand guide is a strand guide roller, pivoting the stand guide roller in unison with the coating material dispenser by pivoting the coating material dispenser about an axis substantially transverse to an axis of the strand guide roller.

18. The method of claim 16, the strand guide coupled to the coating material dispenser by a pivoting guide arm, adjusting a spacing between the strand and the orifice of the coating material dispenser by pivoting the pivoting guide arm.

19. The method of claim 18, the strand guide is a strand guide roller, pivoting the stand guide roller in unison with the coating material dispenser by pivoting the coating material dispenser about an axis substantially transverse to an axis of the strand guide roller.

* * * * *